United States Patent

Subbiah

[11] Patent Number: 5,919,991
[45] Date of Patent: Jul. 6, 1999

[54] SOLID PHASE EXTRACTION OF PHENETHYL ALCOHOL

[76] Inventor: Ven Subbiah, 105 Bella Vista Dr., Edenton, N.C. 27932

[21] Appl. No.: 08/674,918

[22] Filed: Jul. 3, 1996

[51] Int. Cl.[6] .............................. C07C 29/74; C12P 7/22
[52] U.S. Cl. ............................................. 568/810; 435/156
[58] Field of Search .............................. 568/810; 11/702, 11/171; 435/156

[56] References Cited

PUBLICATIONS

Chilla et al., Automated Online Solid–Phase Extration–High–Performance Liquid Chromatagraphy–Diode array Detection of Phenolic Compounds in Sherry Wine, J. Chrommatogr., A 4th International Symposium on Hyphenated Techniques in Chromatography and Hyphen, 1996.

Fabre et al., Extraction of 2–phenylethyl alcohol by Techniques such as adsorption, inclusion, supercritical CO2, liquid–liquid and membrane separations., Perfum. Flavor., pp. 27–28, 30–32, 34, 36–40, 1996.

S. Arctander, Phenylethyl Alcohol, *Perfume and Flavor Chemicals vol. 2*, monograph 2513 (Montclair, N.J., 1969).

R.M.E. Richards and R.J. McBride, The preservation of ophthalmic solutions with antibacterial combinations, *J. Pharm. Pharmac.* 24, 145–48 (1972).

R.M.E. Richards et al., Preservation of fluorescein solutions against contamination with *Pseudomonas aeruginosa*, *J. Pharm. Pharmac.* 21, 681–86 (1969).

G. Fronza et al., Natural Abundance of [2] *H Nuclear Magnetic Resonance Study of the Origin of 2–Phenylethanol and 2–Phenethyl Acetate*, *J. Agric. Food Chem.* 43, 439–443 (1995).

E. Albertazzi et al., Biogeneration of 2–Phenylethanol and 2–Phenylethylacetate Important Aroma Components, *Biotechnology Letters* 16(5), 491–496 (1994).

W.G. Iverson, Ethyl Acetate Extraction of Beer: Quantitative Determination of Additional Fermentation By–Products, *J. Am. Soc. Brew. Chem.* 52(3), 91–95 (1994).

F.R. Gabler, Principles of Tangential Flow Filtration: Applications to Biological Processing, in *Filtration in the Pharmaceutical Industry* (T.H. Meltzer, ed., Marcel Decker Inc., New York (1987).

*Primary Examiner*—Michael L. Shippen
*Attorney, Agent, or Firm*—Myers Bigel Sibley & Sajovec

[57] ABSTRACT

A method for isolating phenethyl alcohol in high yield is provided by fermenting L-phenylalanine within a fermentation bath to provide phenethyl alcohol. The fermented phenethyl alcohol is then contacted with an ion-exchange resin to extract the phenethyl alcohol.

35 Claims, 1 Drawing Sheet

SOLID PHASE EXTRACTION OF PHENETHYL ALCOHOL

The present invention relates to methods for isolating phenethyl alcohol in high yield, and more particularly to methods of extracting phenethyl alcohol from a fermented phenylalanine solution.

BACKGROUND OF THE INVENTION

The production of aroma compounds represents an important tool in the production of natural flavors for food and beverage industries. E. Albertazzi, et al., *Biotech. Lett.* 16, 491–6 (1994). One of the most commonly used aroma compounds is phenethyl alcohol. Phenethyl alcohol (e.g., phenethanol, 2-phenylethanol, or benzeneethanol) is naturally present in many essential oils, and has a rose-like/honey floral odor. Phenethyl alcohol is chemically synthesized or extracted in commercial applications as a flavoring or fragrance for consumer goods, such as perfumes and food.

As a flavorant, phenethyl alcohol is useful in producing a broad range of desirable flavors, especially imitation butter, strawberry, raspberry, caramel, honey, melon and other fruit complexes. S. Arctander, *Perfume and Flavor Chemicals* Vol. 2, 2513 (1969). Phenethyl alcohol is also one of the most widely used of all perfume chemicals, and is particularly desired as a component in perfumes that are characterized as floral, balsamic, Oriental, mossy, herbaceous, or "modern aldehydic." Id. In addition to providing its own distinctive aroma, phenethyl alcohol may be also blended with other aroma compounds (e.g., rose alcohols, lily alcohols, and muguet alcohols) to produce floral scents as well as lime and spice blends. Id. Additionally, phenethyl alcohol is used as an antimicrobial and as a solution preservative. See R. M. E. Richards and R. J. McBride, *J. Pharm. Pharmac.* 24, 145–148 (1972); ibid, 21, 681–686 (1969).

Phenethyl alcohol occurs naturally in alcoholic fermented foods in amounts of 10–100 ppm. M. E. Kieser, et al., *Nature* 204, 887 (1964). This amount, while affecting the quality of alcoholic beverages, is not sufficient as a source for the large-scale production of the natural aroma component. It is therefore of interest to develop methods of producing and isolating phenethyl alcohol in large amounts, and of high purity.

Phenethyl alcohol may be produced by fermenting solutions containing L-phenylalanine under appropriate fermentation conditions. See Albertazzi, et al., supra at 492. Conventional methods of isolating phenethyl alcohol from such fermented solutions generally involve liquid-liquid solvent extraction utilizing high volumes of organic solvents such as butanol. One disadvantage of the solvent extraction technique is the formation of emulsions during extraction, requiring the use of excess solvent and longer times for phase separation. Additionally, the solvent extraction techniques are often cumbersome, and do not provide an optimal yield of final product.

It would be highly desirable to provide a practical and less hazardous method of isolating phenethyl alcohol whereby a high yield of final product is afforded, and the need for large volumes of organic solvent is obviated.

SUMMARY OF THE INVENTION

The present invention relates to a method of isolating phenethyl alcohol from an L-phenylalanine fermentation solution using a solid-phase extraction involving ion-exchange resins.

In particular, a L-phenylalanine solution is prepared. The L-phenylalanine solution is fermented within a fermentation bath, preferably including at least one strain of yeast, to provide phenethyl alcohol. The fermented phenethyl alcohol solution is separated to provide a fermented phenethyl alcohol solution essentially devoid of large molecular-weight molecules, and is preferably separated to provide a fermented phenethyl alcohol solution essentially free of yeast cells. The separated, fermented phenethyl alcohol solution is contacted with an ion-exchange resin to adsorb phenethyl alcohol thereon. After the phenethyl alcohol is adsorbed onto the resin, the resin is eluted with a solvent, and the phenethyl alcohol is collected.

The present invention provides advantages over prior methods of isolating phenethyl alcohol. The rate of recovery is higher when compared to conventional liquid phase extraction techniques, while providing phenethyl alcohol with improved purity. Additionally, the present method avoids cumbersome extraction and separation, particularly with butanol, thus also avoiding the common problem of emulsion formation during extraction and reducing the need for high volumes of unwieldy and potentially hazardous organic solvents.

DETAILED DESCRIPTION OF THE INVENTION

Figure 1:
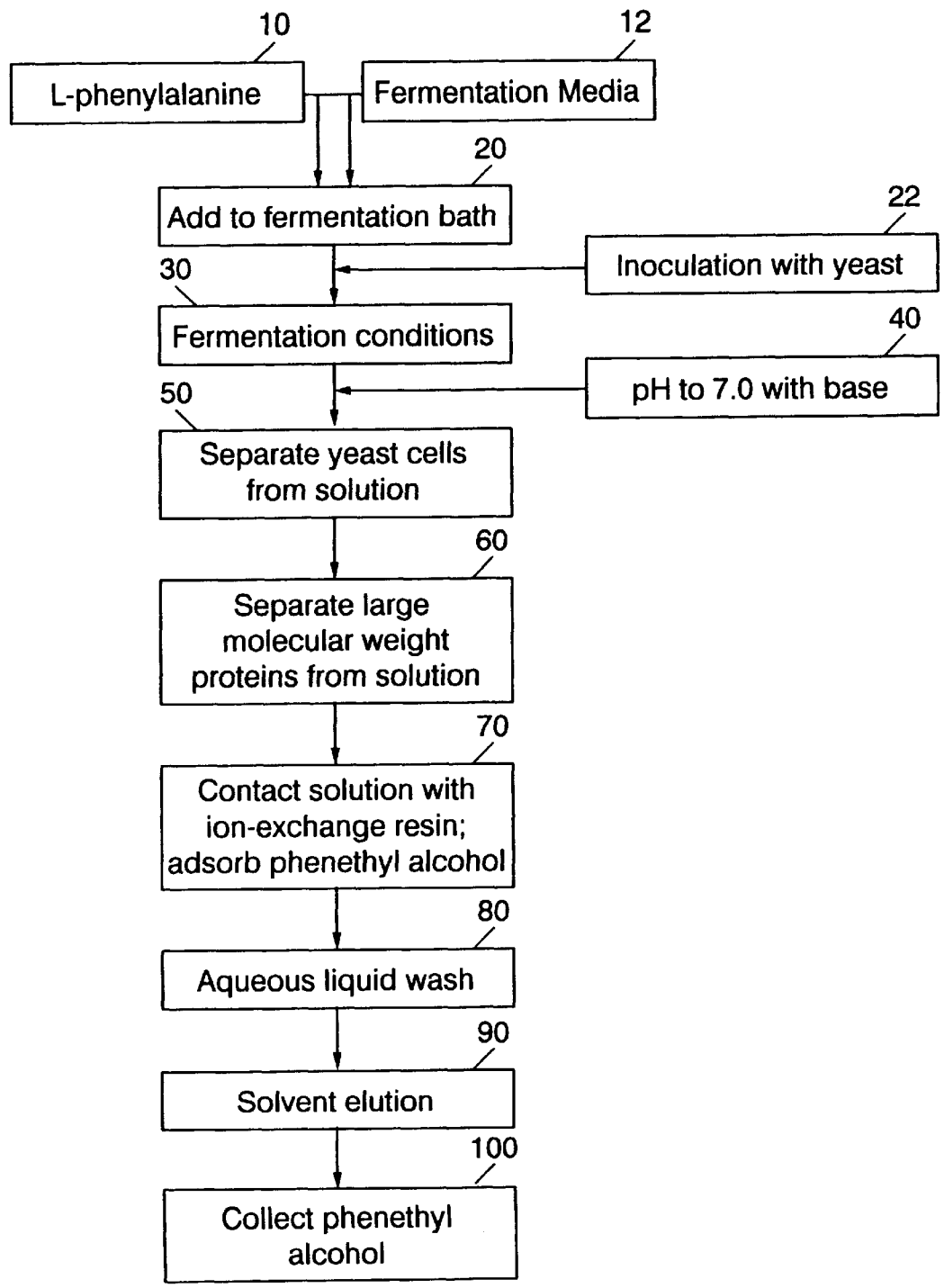
FIG. 1 is a schematic diagram of process steps representative of one embodiment of the present invention.

Referring to FIG. 1, L-phenylalanine is provided as a solution 10, wherein the solution comprises fermentation media 12 containing L-phenylalanine. Alternatively, the fermentation media is combined with a solution of L-phenylalanine. The combined fermentation solution is added 20 to a fermentation bath, which fermentation bath is then inoculated with at least one species of yeast 22. The pH of the fermentation solution is adjusted 40 to a pH of about 7.0 with a base (e.g., NaOH) after which the fermentation solution is allowed to ferment under fermentation conditions 30, providing phenethyl alcohol.

The fermented phenethyl alcohol mixture, namely the phenylalanine and fermentation media mixed with yeast cells, is then separated 50 to provide a fermented phenethyl alcohol solution essentially devoid of yeast cells. The essentially yeast-free, fermented phenethyl alcohol mixture is then further separated 60 to provide a fermented phenethyl alcohol solution essentially devoid of large molecular weight molecules. As used herein, a large-molecular weight molecule refers to a molecule that is larger than about 10 kilodaltons (10 K), and is preferably larger than about 20 kilodaltons. Examples of such molecules include polysaccharides, high molecular weight peptides and proteins, and the like.

The phenethyl alcohol solution devoid of large molecular weight molecules is then contacted with an ion-exchange resin 70 to adsorb the phenethyl alcohol to the resin. The ion-exchange resin is then washed 80 at least once with an aqueous liquid, and is then further eluted 90 with a solvent. Finally, the phenethyl alcohol is collected 100 from the elution volume.

Prior to extraction, the ion-exchange resin may be activated by washing the resin with an aqueous liquid, and then with one or more solvents.

L-phenylalanine is widely commercially available in powdered form. Solutions of L-phenylalanine may be provided by dissolving L-phenylalanine in an appropriate solvent. Preferably, the L-phenylalanine solution is provided by dissolving the L-phenylalanine using a liquid having an aqueous character. Such a liquid consists primarily of water, normally greater than about 90 percent water, and can be essentially pure water in certain circumstances. For example, a solvent having an aqueous character can be distilled water, tap water or the like. However, a solvent having an aqueous character can include water having substances such as pH buffers, pH adjusters, organic and inorganic salts, or surfactants incorporated therein. The solvent can also be a co-solvent mixture of water and minor amounts of one or more other solvents (e.g., methanol, ethanol) which are miscible therewith.

In one embodiment of the invention, the L-phenylalanine solution is provided as a fermentation media solution containing L-phenylalanine. Alternatively, an L-phenylalanine solution may be prepared separately from a fermentation media solution, and then added to the fermentation media solution. The fermentation media solution may contain components essential to the proper fermentation of L-phenylalanine, which components will be apparent to one skilled in the art. In a preferred embodiment of the invention, the fermentation media contains dextrose monohydrate, $K_2HPO_4$, and $KH_2PO_4$, and is adjusted prior to fermentation to a pH of about 6.5 with a base (e.g., NaOH).

The L-phenylalanine solution, preferably an aqueous L-phenylalanine solution, is fermented in a fermentation bath under fermentation conditions. The basic reaction involves the decomposition of the amino acid into an alcohol and carbon dioxide. The fermentation reaction is induced by a living organism or enzyme, specifically microorganisms occurring in one-celled plants (i.e. yeast, mold or fungi). Preferably, the L-phenylalanine solution is fermented in a fermentation bath including at least one strain of yeast. Preferred yeasts include strains of the genera Hansenula (e.g., *H. anomala*), Pichia (e.g., *P. pastoris, P. etchelsii*), Kloeckera (e.g., *K. saturnus*), Klyveromyces (e.g., *K. fragilis*), and Saccharomyces (e.g., *S. distaticus, S. delbrueckii*, and *S. cerevisiae*), sometimes referred to as "brewer's yeast." Most commercially available yeast such as Fleischmann's Yeast, Red Star yeast, Ale Beer Yeast, Geordie yeast, Montrachet yeast, Laaglander Irish ale yeast, etc. are mixtures of various yeast strains.

Typically the L-phenylalanine solution is fermented at ambient or room temperature over a period of at least one day, and up to about fifteen days or more. In the resulting fermented L-phenylalanine solution, phenethyl alcohol typically comprises at least about 60% of the fermented solution by weight, and preferably at least about 80% of the fermented solution by weight, as measured by a commercially available vinometer.

Yeast cells are removed from the fermented solution by any appropriate filtration or separation techniques which will be readily apparent to one skilled in the art of fermentation. In a preferred embodiment, yeast cells are removed by crossflow filtration, utilizing a filter with a pore size of not more than 0.2 $\mu$m and preferably not more than 0.15 $\mu$m.

Large molecular-weight molecules are removed from the fermented solution by any appropriate filtration or separation techniques which will be readily apparent to one skilled in the art of protein separation. In a preferred embodiment, large molecular-weight molecules are also removed by crossflow filtration, utilizing a filter with a pore size of not more than about 10 kilodaltons (K).

Preferably, the ion-exchange resin is immobilized onto a column, the use and selection of which will be apparent to one in the art. Ion-exchange columns are packed with small beads that carry either a positive or a negative charge, such that compounds are fractionated according to the arrangement of charge on their surface. In an ion-exchange column, the matrix or resin is insoluble and carries ionic charges that retard molecules of the opposite charge. The strength of the association between the dissolved molecules and the ion-exchange matrix depends on both the ionic strength and the pH of the eluting solution, which may therefore be varied in a systematic fashion to achieve effective separation.

In a preferred embodiment, the resin comprises polymeric beads packed onto a column. The beads may comprise polymers of, e.g., styrene, styrene divinylbenzene, methacrylate, propylene, or derivatives and combinations thereof. In one preferred embodiment, the beads comprise polymers of styrene divinylbenzene. The polymeric beads may be as large as 600 $\mu$m in diameter, preferably as large as 400 $\mu$m in diameter, and more preferably as large as 250 $\mu$m in diameter. In a more preferred embodiment, the resin used is Diaion HP 20 (Mitsubishi Kasei America, Inc., White Plains, N.Y.), a macroporous styrenic-based polymeric bead type resin.

After the phenethyl alcohol has been allowed to adsorb onto the ion-exchange resin, the resin may be washed with deionized water. The phenethyl alcohol may then be eluted from the resin by repeated washing with solvents. Preferred solvents include acetone, methanol, ethanol, with ethanol and methanol being particularly preferred.

The phenethyl alcohol isolated by any embodiment of the present invention is useful as a fragrance or as a flavoring in foods and beverages, and primarily in non-alcoholic beverages.

The following examples are provided in order to further illustrate various embodiments of the invention and are not to be construed as limiting the scope thereof. In the following examples, lbs. means pounds, $\mu$m means micrometers, cm means centimeters, $\mu$L means microliters, mL means millilters, L means liters, ppm means parts per million, °C. means temperature in degrees Centigrade, and $dH_2O$ means deionized water.

EXAMPLE 1

Fermentation and Filtration of Phenylalanine

Six hundred and forty-two (642) lbs. of dextrose monohydrate is added to a fermentation bath containing 700 gallons of water heated to a temperature of 30° C. This mixture is stirred until the dextrose monohydrate is dissolved. Forty-four (44) lbs. of L-phenylalanine (Fisher Scientific, Raleigh, N.C.) is added to the solution, along with 9.9 lbs. of $K_2HPO_4$ and 5.4 lbs of $KH_2PO_4$. The solution is stirred until all solutes have dissolved, after which NaOH (25% solution) is added until the pH of the fermentation solution is 4.5. The fermentation solution is then inoculated with 58.4 lbs. (approximately 0.08 pounds/gallon) of Red Star Dry Yeast and allowed to ferment under aeration and agitation conditions for 24 hours.

After fermentation, the pH of the fermented solution is adjusted to pH 7.0 with NaOH (25% solution). The solution is then transferred to a crossflow filtration tank and run, with pressure, through a crossflow Maxcell® filter of pore size 0.2 $\mu$m (A/G Technology Corporation, Boston, Mass.) to remove yeast cells. After this first filtration, the resulting essentially yeast-free fermented solution is then run through another crossflow Maxcell filter of pore size 10 kilodaltons to remove large molecular weight molecules.

COMPARATIVE EXAMPLE A

Solvent Extraction of Phenethyl Alcohol

Phenethyl alcohol was isolated using conventional liquid-phase solvent extraction techniques. Additionally, different solvents that are used in the conventional method were compared, as measured by the yield of phenethyl alcohol provided when each solvent was used to extract phenethyl alcohol.

Two liters of fermented L-phenylalanine was collected from a large fermenter. Two hundred mL aliquots of the fermented solution were extracted three times with an equal volume of one of the following solvents: hexane, ethyl ether, ethyl acetate, or butanol. The organic phase of each solvent was pooled and concentrated by evaporating the solvent to near dryness. Additionally, solvent from the trap, as well as left-over aqueous fractions were collected for quantitative analysis.

Individual collected samples were analyzed by gas chromatography (injection volume, 1 μL of respective solvent or aqueous fractions) for quantitative estimation of concentration of phenethyl alcohol present in each fraction. The results are presented below:

| Sample | Phenethyl alcohol (ppm) |
| --- | --- |
| Original fermented broth (no extraction) | 2376 |
| 200 ml Hexane extraction | 1995 |
| trap fraction | 692 |
| hexane/aqueous | 833 |
| 200 mL Ethyl ether extraction | 2582 |
| ethyl ether/aqueous | 462 |
| 200 mL Ethyl acetate extraction | 3715 |
| ethyl acetate trap | 323 |
| ethyl acetate/aqueous | 8.0 |
| 200 mL Butanol extraction | 2441 |
| butanol trap | 222 |
| butanol/water | 2.5 |

These results indicate that when conventional liquid-phase solvent extraction techniques are used to isolate phenethyl alcohol, ethyl acetate appears to provide the highest concentration of phenethyl alcohol. However, the undesired formation of phenethyl acetate is a disadvantage in terms of the practical use of ethyl acetate in phenethyl alcohol extraction. Furthermore, under neutral pH (7.0) ethyl acetate is known to be non-reactive.

Butanol is an often-used solvent in the conventional practice of phenethyl alcohol extraction, and these results indicate that it extracts phenethyl alcohol in a concentration of approximately 2400 parts per million (ppm).

COMPARATIVE EXAMPLE B

Solid Phase Extraction of Phenethyl Alcohol

Phenethyl alcohol was isolated using one method of the present invention in order to compare the efficacy of the method with conventional methods in terms of final yield of phenethyl alcohol.

500 mL of fermented L-phenylalanine was collected from a large fermentor. The HP-20 ion-exchange resin (Mitsubishi Kasei Corp., White Plains, N.Y.) was packed on a column (2.5×30 cm) and activated by passing 2 bed-volume each of acetone and methanol over the resin. The gel was rinsed with deionized water and remained wet prior to extraction. The organic molecules were adsorbed onto the gel by passing the aqueous fermented solution through the gel. Subsequently, the gel was eluted with 1 L of deionized water, followed by 1 L each of methanol and acetone.

An aliquot of each collected fraction was directly injected into a gas chromatograph for quantitative phenethyl alcohol determination.

| Elution fraction | Quantity | Phenethyl alcohol (ppm) |
| --- | --- | --- |
| HP 20 wash-direct | 500 mL | 3.0 |
| DI water | 1000 mL | 0.0 |
| Methanol | 1000 mL | 3014 |
| Methanol/acetone | 1000 mL | 60 |

These results indicate that after adsorbing onto the ion-exchange resin, phenethyl alcohol is eluted from the resin with methanol in a concentration of approximately 3000 parts per million, which is a concentration of approximately 20 percent greater than that achieved with conventional butanol extraction.

EXAMPLE 2

Activation of HP-20 Gel

One particular advantage of using the ion exchange resin is that the resin may be reactivated after use in order to be utilized repeatedly for the purpose of isolating phenethyl alcohol.

In order to activate the HP-20 gel, approximately 1.5 L of HP-20 gel was stirred in 3 L of acetone, and after settling, the acetone was decanted to remove the fines. The support was transferred to a 3 L coarse fitted filter and was washed successively with methanol (2 L), water (2 L), 30% w/v potassium hydroxide, water (4 L), 10% hydrochloric acid (2 L), water (until effluent was neutral), acetone (4 L), methanol (4 L) and water (4 L). Using this process, the HP-20 gel is available for reuse repeatedly.

EXAMPLE 3

Comparative Ethanol Washes of Resin

Phenethyl alcohol was isolated onto an ion exchange resin using the method described above in Comparative Example B. However, instead of methanol, ethanol in varying concentrations was used to elute the column in order to evaluate the effectiveness of ethanol as a solvent in the practice of the present invention. These results are presented below.

| Elution | Volume (mL) | Phenethyl alcohol (ppm) |
| --- | --- | --- |
| fermented broth | 1000 | 2377 |
| HP-20 wash | 1000 | 10 |
| dH20 wash | 1000 | 3 |
| 10% ethanol | 500 | 0 |
| 25% ethanol | 500 | 0 |
| 50% ethanol | 500 | 0 |
| 100% ethanol | 500 | 3457 |

These results indicate that ethanol is useful in the practice of the present invention as a solvent for eluting phenethyl alcohol that has been adsorbed onto an ion-exchange resin.

In the specification and examples, there have been disclosed preferred embodiments of the invention. Although specific terms are employed in these examples, they are used in a generic and descriptive sense only and not for the purpose of limitation, the scope of the invention being defined by the following claims.

That which is claimed is:

1. A process for preparing phenethyl alcohol comprising:
   (a) providing an L-phenylalanine solution;
   (b) fermenting the L-phenylalanine solution within a fermentation bath to provide a fermented phenethyl alcohol solution;
   (c) separating the phenethyl alcohol solution to provide a fermented phenethyl alcohol solution essentially devoid of large molecular-weight molecules;
   (d) isolating the fermented phenethyl alcohol solution essentially devoid of large molecular-weight molecules;
   (e) contacting the fermented phenethyl alcohol solution of step (d) with an ion-exchange resin under conditions sufficient to adsorb phenethyl alcohol thereon; and
   (f) collecting the phenethyl alcohol.

2. The process according to claim 1, whereby the L-phenylalanine solution is a liquid having an aqueous character.

3. The process according to claim 1, whereby the L-phenylalanine solution comprises a fermentation media solution containing L-phenylalanine.

4. The process according to claim 1, whereby the L-phenylalanine solution is added to a fermentation media solution to provide a fermentation media solution containing L-phenylalanine.

5. The process according to claim 1, whereby said fermenting step comprises the addition of at least one strain of yeast.

6. The process according to claim 5, whereby the yeast is selected from the group consisting of strains of kluyveromyces and Saccharomyces.

7. The process according to claim 5, further comprising the additional step of separating the fermented phenethyl alcohol solution to provide a fermented phenethyl alcohol solution essentially free of yeast cells.

8. The process according to claim 7, whereby said additional separation step comprises crossflow filtration.

9. The process according to claim 1, whereby the fermentation bath is a liquid having an aqueous character.

10. The process according to claim 1, whereby the L-phenylalanine solution is fermented over a period of at least 24 hours.

11. The process according to claim 1, whereby the L-phenylalanine solution is fermented to provide a fermented phenethyl alcohol solution having a phenethyl alcohol content of at least 60% by weight.

12. The process according to claim 1, whereby said separation step comprises crossflow filtration.

13. The process according to claim 1, wherein said contacting step comprises contacting the fermented phenethyl alcohol solution with an ion-exchange resin comprising polymeric beads of average particle size not greater than 250 $\mu$m in diameter.

14. The process according to claim 1, whereby the ion exchange resin is activated prior to said contacting step.

15. The process according to claim 14, whereby said activation comprises washing the ion exchange resin first with deionized water and then with a solvent.

16. The process according to claim 15, whereby said solvent is selected from the group consisting of ethanol, methanol, and acetone.

17. The process according to claim 1, further comprising washing the resin adsorbed to phenethyl alcohol with deionized water prior to the collection step.

18. The process according to claim 1, whereby said collecting step comprises repeated washings of the ion exchange resin with a solvent.

19. The process according to claim 18, whereby said solvent is selected from the group consisting of ethanol, methanol, and acetone.

20. A process for preparing phenethyl alcohol having a high yield, the process comprising:
   (a) preparing a L-phenylalanine solution;
   (b) fermenting the L-phenylalanine solution within a fermentation bath containing at least one strain of yeast to provide a fermented phenethyl alcohol solution;
   (c) separating the phenethyl alcohol solution to provide a fermented phenethyl alcohol solution essentially devoid of yeast cells;
   (d) separating the phenethyl alcohol solution essentially devoid of yeast cells to provide a fermented phenethyl alcohol solution essentially devoid of large molecular-weight molecules;
   (e) isolating the fermented phenethyl alcohol solution essentially devoid of large molecular-weight molecules;
   (f) contacting the fermented phenethyl alcohol solution of step (e) with an ion-exchange resin to adsorb phenethyl alcohol thereon; and
   (g) collecting the phenethyl alcohol.

21. The process according to claim 20, whereby the L-phenylalanine solution is a liquid having an aqueous character.

22. The process according to claim 20, whereby the L-phenylalanine solution comprises a fermentation media solution containing L-phenylalanine.

23. The process according to claim 20, whereby the L-phenylalanine solution is added to a fermentation media solution to provide a fermentation media solution containing L-phenylalanine.

24. The process according to claim 20, whereby the yeast is selected from the group consisting of strains of Kluyveromyces and Saccharomyces.

25. The process according to claim 20, whereby said first separation step comprises crossflow filtration.

26. The process according to claim 20, whereby said second separation step comprises crossflow filtration.

27. The process according to claim 20, whereby the fermentation bath is a liquid having an aqueous character.

28. The process according to claim 20, whereby the L-phenylalanine solution is fermented over a period of at least 24 hours.

29. The process according to claim 20, whereby the L-phenylalanine solution is fermented to provide a fermented phenethyl alcohol solution having a phenethyl alcohol content of at least 60% by weight.

30. The process according to claim 20, whereby the ion exchange resin is activated prior to said contacting step.

31. The process according to claim 30, whereby said activation comprises washing the ion exchange resin first with deionized water and then with a solvent.

32. The process according to claim 31, whereby said solvent is selected from the group consisting of ethanol, methanol, and acetone.

33. The process according to claim 20, further comprising washing the resin adsorbed to phenethyl alcohol with deionized water prior to the collection step.

34. The process according to claim 20, whereby said collecting step comprises repeated washings of the ion exchange resin with a solvent.

35. The process according to claim 34, whereby said solvent is selected from the group consisting of ethanol, methanol, and acetone.

* * * * *